(12) United States Patent
Järverud

(10) Patent No.: US 7,190,996 B2
(45) Date of Patent: *Mar. 13, 2007

(54) MONITOR FOR EARLY DETECTION OF ISCHEMIC HEART DISEASE

(75) Inventor: Karin Järverud, Solna (SE)

(73) Assignee: St. Jude Medical AB, Jarfalla (SE)

( * ) Notice: Subject to any disclaimer, the term of this patent is extended or adjusted under 35 U.S.C. 154(b) by 546 days.

This patent is subject to a terminal disclaimer.

(21) Appl. No.: 10/620,199

(22) Filed: Jul. 14, 2003

(65) Prior Publication Data
US 2004/0087870 A1   May 6, 2004

(30) Foreign Application Priority Data
Jul. 22, 2002   (SE) ..................... 0202290

(51) Int. Cl.
*A61B 5/03* (2006.01)
*A61B 5/04* (2006.01)

(52) U.S. Cl. ............ 600/547; 600/481; 600/483; 600/508; 600/515; 600/526; 128/920; 128/923

(58) Field of Classification Search ........ 128/920–923; 600/481, 483, 508, 547, 515, 526; 607/8, 607/28
See application file for complete search history.

(56) References Cited

U.S. PATENT DOCUMENTS

| | | | | |
|---|---|---|---|---|
| 4,905,696 A | * | 3/1990 | Amundson et al. | 607/9 |
| 4,905,705 A | * | 3/1990 | Kizakevich et al. | 600/509 |
| 5,178,154 A | * | 1/1993 | Ackmann et al. | 600/526 |
| 5,282,840 A | * | 2/1994 | Hudrlik | 607/28 |
| 5,427,112 A | * | 6/1995 | Noren et al. | 600/515 |
| 5,735,286 A | * | 4/1998 | Notton et al. | 600/513 |
| 6,473,640 B1 | | 10/2002 | Erlebacher | 600/547 |
| 6,827,690 B2 | * | 12/2004 | Bardy | 600/508 |

FOREIGN PATENT DOCUMENTS

| | | |
|---|---|---|
| EP | 0 607 511 | 7/1994 |
| EP | 0 615 770 | 9/1994 |

(Continued)

OTHER PUBLICATIONS

Jarverud, K. et al., "Analysis of the O-wave in acute right ventricular apex impedance measurements with a standard pacing lead in animals," Jul. 17, 2002, Medical & Biological Engineering & Computing 2002, vol. 40, pp. 512-519.*

(Continued)

*Primary Examiner*—Robert E. Pezzuto
*Assistant Examiner*—Natasha Patel
(74) *Attorney, Agent, or Firm*—Schiff Hardin LLP

(57) ABSTRACT

A monitor for early detection of an ischemic heart disease of a patient has an impedance measurement unit including an electrode arrangement for measuring an intracardiac impedance and generating a corresponding impedance signal, a notch detector connected to the impedance measurement unit for detecting the occurrence of a notch in the impedance signal coincident with the entry of blood into the ventricle, and a pattern recognition unit which compares the measured post-notch impedance curve with a stored predetermined reference impedance curve template to detect an ischemic heart disease from the result of the comparison.

22 Claims, 6 Drawing Sheets

FOREIGN PATENT DOCUMENTS

| | | |
|---|---|---|
| EP | 1 238 630 | 9/2002 |
| WO | WO 02/43587 | 6/2002 |

OTHER PUBLICATIONS

"Usefulness of the Impedance Cardiogram to Reflect Left Ventricular Diastolic Function," Pickett et al. The American Journal of Cardiology, vol. 71, May 1, 1993, pp. 1099-1103.

"Analysis Of The O-Wave In Acute Right Ventricular Apex Impedance Measurements With A Standard Pacing In Animals," Järverud et al., Med. Biol. Eng. Comput. 2002, vol. 40, pp. 512-519.

"The Minnesota Impedance Cardiograph—Theory and Applications," Kubicek et al., Biomedical Engineering, Sep. 1974, pp. 410-416.

* cited by examiner

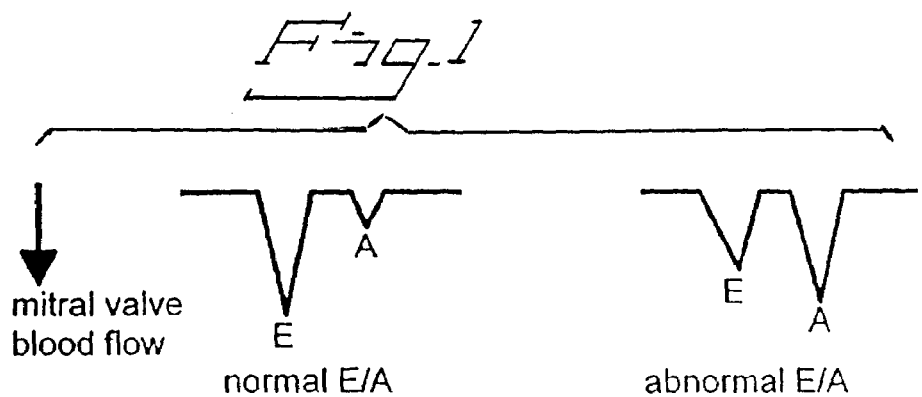
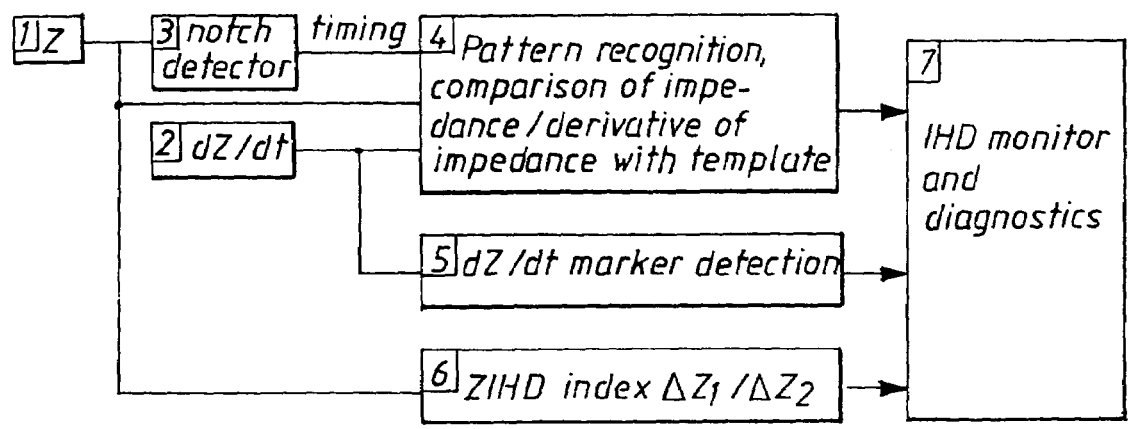

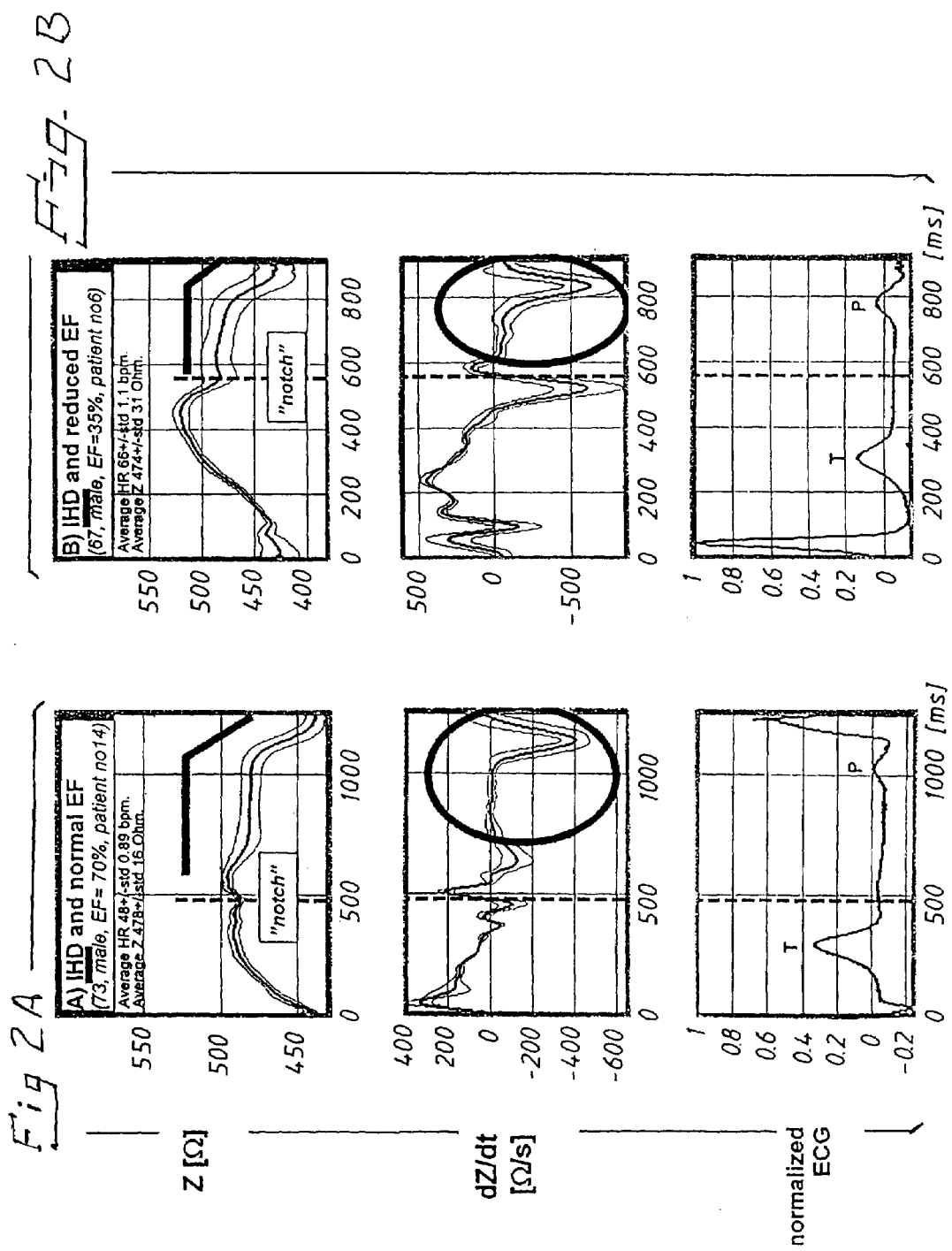

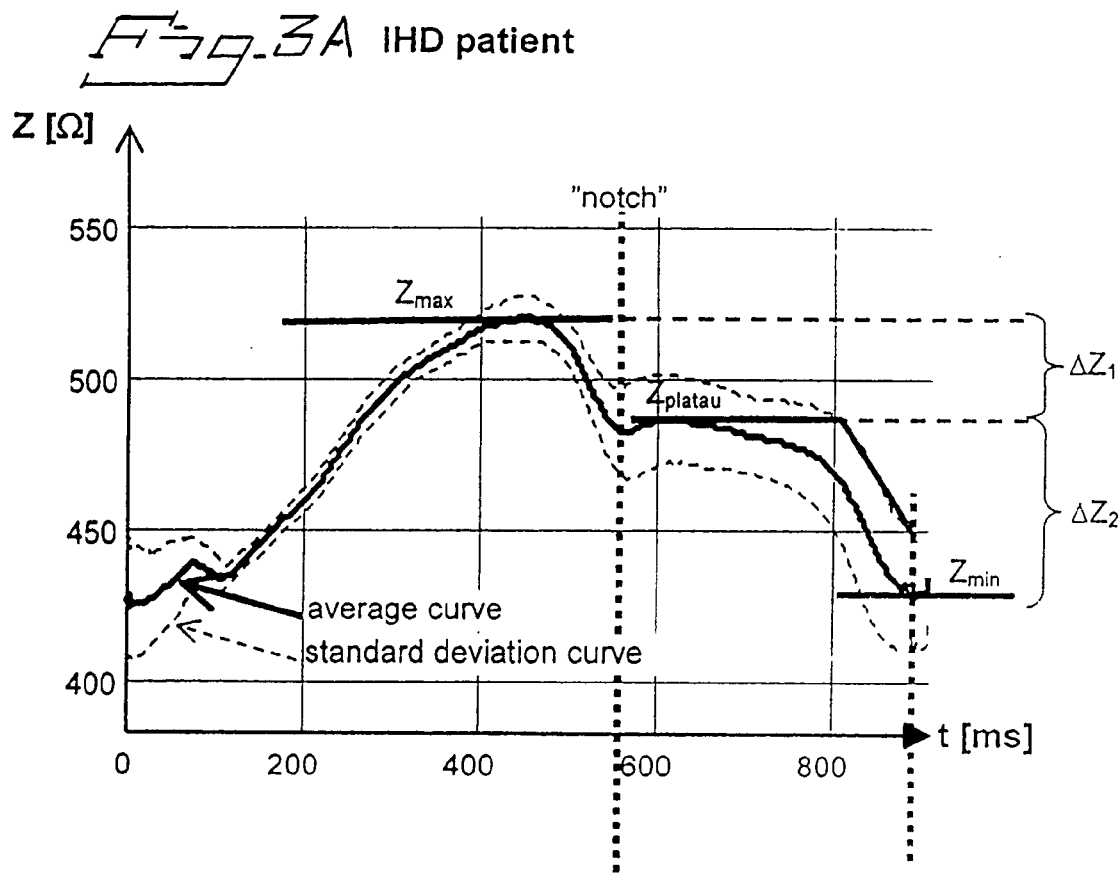
Fig. 3A  IHD patient
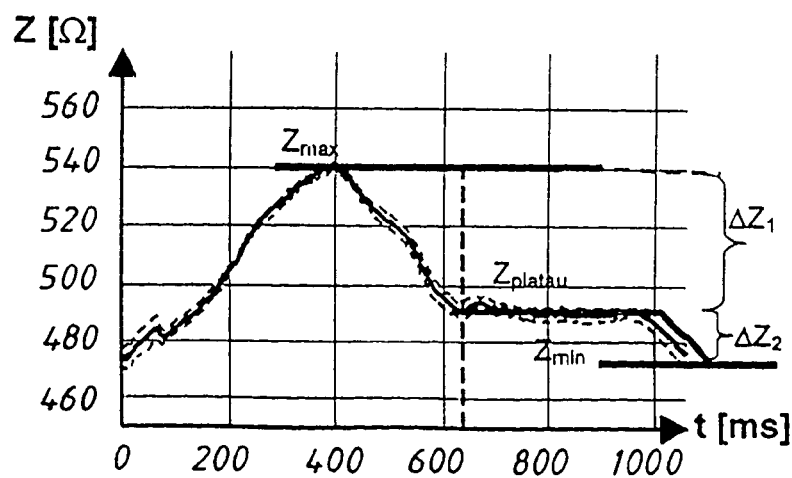
Fig. 3B  Healthy patient

MONITOR FOR EARLY DETECTION OF ISCHEMIC HEART DISEASE

BACKGROUND OF THE INVENTION

1. Field of the Invention

The present invention relates to a monitor for early detection of an ischemic heart disease of a patient, of the type having comprising an impedance measurement unit including an electrode arrangement for measuring an intracardiac impedance and generating a corresponding impedance signal, and a notch detector connected to the impedance measurement unit that detects the occurrence of a notch in the impedance signal coincident with the entry of blood into the ventricle.

2. Description of the Prior Art

A monitor of the above-defined type is described in PCT Application WO 02/43587.

Congestive heart failure (CHF) is a fast growing health problem that mostly affects only adults. In this condition the heart is unable to pump enough blood to meet the need of the body's organs. Among the most common causes of CHF are coronary artery disease, causing myocardial ischemia, myocardial infarction and cardiomyopathy. During ischemia the cardiac relaxation, i.e. diastolic, is changed or disturbed because the cardiac muscle is stiffened. A disturbed diastolic phase or diastolic failure is a very early kind of congestive heart failure, such that at this early state it might not even appear as symptoms to the patient. Detection of these early signs of disturbed relaxation patterns is described in the above-mentioned PCT Application WO 02/43587.

Early detection of ischemic heart disease (IHD) is required since that will give opportunities to prevent life threatening complications. By using a parameter such as diastolic intracardiac impedance IHD will be detected at a much earlier stage and myocardiac consequences such myocardial infarction (MI) and CHF may be prevented.

IHD prevents normal cardiac function because oxygen supply to the cardiac muscle is too low. In the acute stage of global cardiac ischemia (after 1–2s), relaxation failure occurs in the diastole (filling phase) as the myocardial tissue stiffens from lack of oxygen, followed by contraction failure (after 10s), increased filling pressures (after 20 s), changes in ECG (after 25 s) and angina (30 s). Even if global ischemia ceases after a few seconds and oxygen supply is fully recovered, the disturbed relaxation may remain for hours or days. The diastolic portion of the cardiac cycle seems to be the most sensitive parameter for IHD since it is effected first and residue effects remain for a long period after oxygen supply is restored. Cardiac tissue stiffness caused by IHD prevents adequate passive ventricular filling. The heart will try to compensate for this decreased filling by a largely increased atrial contraction. The atrial contribution to the ventricular filling in relation to passive filling will thus increase and this is often seen as an inverted early filling/ Atrial contribution (E/A) quotient in echo-cardiographical measurements of mitral blood flow. FIG. 1 shows schematically the early filling E and the atrial contribution A of mitral value blood flow for a normal healthy heart and an abnormal heart suffering from IHD.

When IHD progresses it may lead to MI, CHF and/or the patient's death. In fact early detection of IHD can serve as an early marker for CHF risk factor.

Detection of the start of the diastolic phase by a "notch" detection is described in the above mentioned PCT Application WO 02/43587, cf. also Brian R. Pickett et. al., The American Journal of Cardiology, Vol. 71, May 1, 1993, "Usefulness of the Impedance Cardiogram to Reflect Left Ventricular Diastolic Function", which describes a study of the correlation between a dip in a non-invasively measured impedance and Doppler measurements for diastolic studies showing the appearance of a notch in the impedance signal corresponding to early diastole of a cardiac cycle.

SUMMARY OF THE INVENTION

The intracardiac impedance reflects the blood volume in the heart chambers, and thus an object of the present invention is to provide a monitor for early detection of an ischemic heart decease of the type described above wherein the measured intracardiac impedance curve during a selected portion of the cardiac cycle related to the notch is analyzed.

The above object is achieved in accordance with the present invention in a monitor of the type described above having a pattern recognition unit that compares a portion of the impedance curve occurring after the notch (post-notch impedance curve) with a stored predetermined reference impedance curve template, to detect an ischemic heart disease as a result of the comparison.

The above discussed increased stiffness of the heart tissue caused by IHD is reflected in the shape of the post-notch portion of the measured impedance curve and this phenomena is thus utilized in the monitor according to the invention for early detection of a ischemic heart decease.

Generally the impedance curve has a plateau after the notch, which for IHD patients is followed by a dominating decrease coinciding with atrial contraction, indicating that the atria of these IHD patients are trying to compensate for the reduced passive ventricular filling. To detect this decrease, in an embodiment of the monitor of the invention, a differentiating unit is provided to calculate the time derivative, dZ/dt, of the impedance curve, and the pattern recognition unit compares the shape of the time derivative in the post notch portion of the impedance curve with a predetermined reference impedance derivative template.

In another embodiment of the monitor according to the invention a calculation unit calculates, for each cardiac cycle, an ischemic heart decease index, ZIHD-index, defined by $$ZIHD\text{-index} = \Delta Z_1 / \Delta Z_2$$

where $\Delta Z_1$ denotes, for each cardiac cycle, the difference between a maximum value of the measured impedance and the impedance value measured in a plateau occurring in the impedance curve after the notch, and $\Delta Z_2$ denotes the difference between the impedance value in the plateau and a minimum value of the measured impedance in an impedance decrease following the plateau, for detecting an ischemic heart disease from the calculated ZIHD-index. The ZIHD-index indicates the ratio between the passive filling and the contribution from the atrium to the ventricle filling. With the ZIHD-index the progression and degree of IHD can be monitored and the degree of cardiac compensation for the IHD can be calculated. The more the atrium is compensating for reduced passive ventricular filling the more advanced is the IHD. Atrial compensation is feasible only to a certain point and the more IHD progresses the more enlarged the atrium will become and the risk of atrial defibrillation AF is increased. By monitoring the ZIHD-index development of AF problems can be avoided. Alternatively to the monitoring of the ZIHD-index a first comparison means can be provided to compare the absolute value $|\Delta Z_1|$ of $\Delta Z_1$ and/or the absolute value $|\Delta Z_2|$ of $\Delta Z_2$ with a predetermine $\Delta Z_1$ threshold value and/or a predetermined $\Delta Z_2$ threshold value respectively. $\Delta Z_2$ is a measure of the function of the atrium and by monitoring $\Delta Z_2$ it is possible to observe how the disease is advancing.

The post-notch plateau is not always a horizontal plateau and some patients have an overshoot after the notch. It is therefore advantageous, in another embodiment of the monitor according to the invention, to provide a first averaging unit to determine an average value of the measured impedance curve in a predetermined time window after the notch for use as a plateau impedance value. The delay of the window after the notch is selectable and the length of the time window is preferably in the range of 100–150 msec.

In another embodiment of the monitor according to the invention a loop generator is connected to the impedance measurement unit and to the differentiating unit to receive the impedance signal and the first time derivative dZ/dt of the impedance signal for plotting impedance values against related time derivative values to form a loop for each cardiac cycle. A third comparison unit is connected to the loop creator for comparing the loop with a predetermined loop template to detect an ischemic heart disease from the result of the comparison. This comparison unit preferably compares the shape of the loop in the part of the loop that corresponds to the post-notch portion of the impedance curve, with the corresponding part of the loop template. By analyzing such a loop very clear indications can be obtained of deviations indicating an ischemic heart disease.

In a further embodiment of the monitor according to the invention an averaging unit is connected to the impedance measuring unit for determining an average impedance signal of impedance signals measured during a predetermined number of cardiac cycles, and the pattern recognition unit is connected to the this averaging unit to compare the average value of the post-notch impedance curves with the reference impedance curve template. Another averaging unit can be connected to the differentiating unit for determining an average time derivative of impedance signals measured during a predetermined number of cardiac cycles. The pattern recognition unit is connected to the this averaging unit to compare the average time derivative of the post-notch portion of the measured impedance curves with corresponding part of the reference impedance derivative template. The loop generator preferably is connected to these averaging units to receive the average impedance signal and average time derivative to form a corresponding average loop, and the comparison unit compares the average loop with the predetermined loop template. By using average quantities in this way in the detection of an ischemic heart disease the reliability in the detection can be still improved.

DESCRIPTION OF THE DRAWINGS

FIG. 1, as discussed above, shows the ratio between the early passive filling and the atrial contribution to the mitral valve blood flow for a normal heart, and for an abnormal heart suffering from an ischemic heart disease.

FIGS. 2A, 2B, 2C and 2D show results of impedance measurements in four different subjects, respectively.

FIGS. 3A and 3B show the average value and standard deviation, respectively, for a number of impedance measurements.

FIG. 5 is a block diagram of an embodiment of a monitor for early detection of ischemic heart disease in accordance with the invention.

DESCRIPTION OF THE PREFERRED EMBODIMENTS

Figures 2C, 2D:
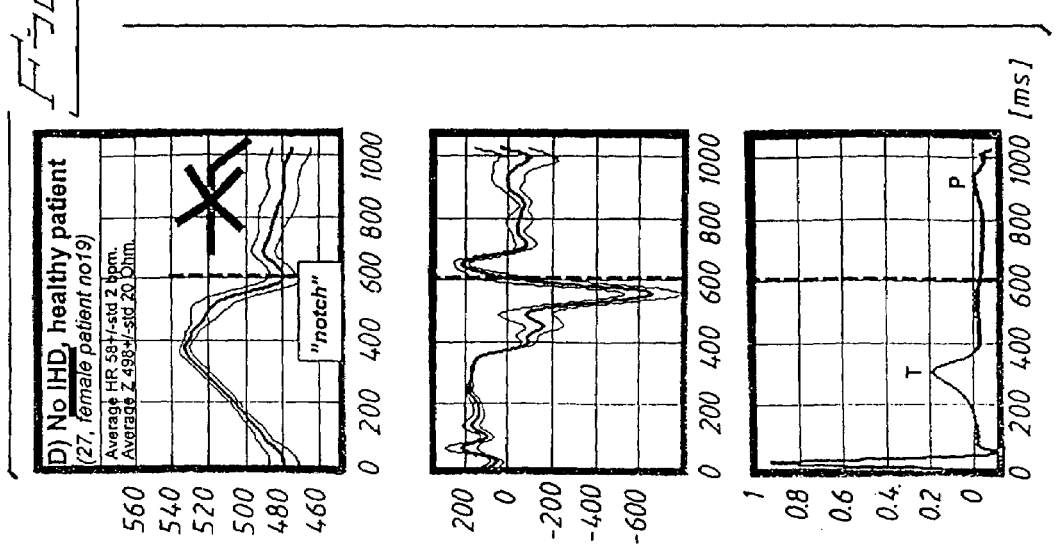
Figure 4A:
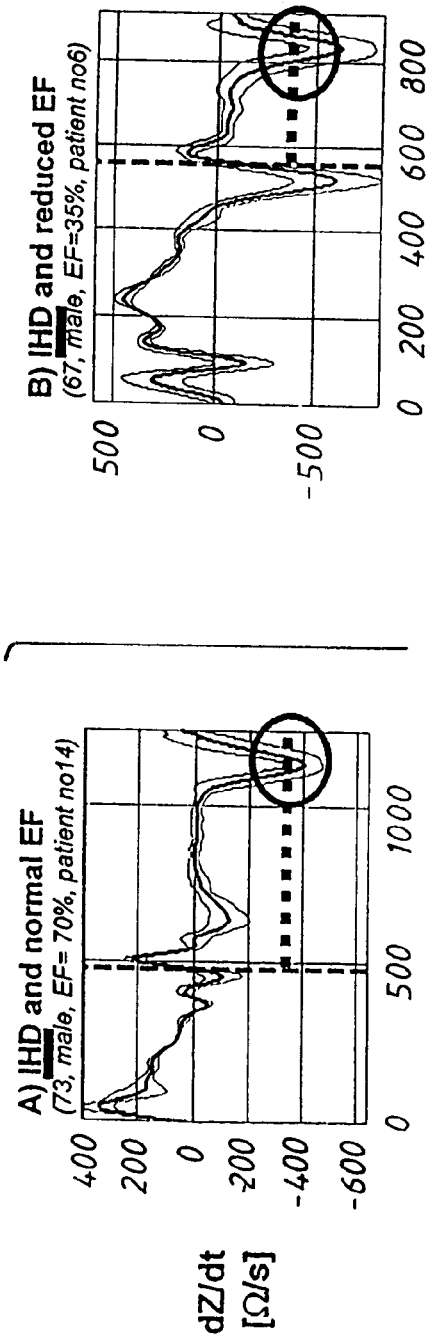
FIGS. 4A, 4B, 4C and 4D show the use of the first time derivative of the impedance curve for detecting an ischemic heart disease in the four subjects whose impedance measurements are shown in FIGS. 2A, 2B, 2C and 2D.
Figure 4B:
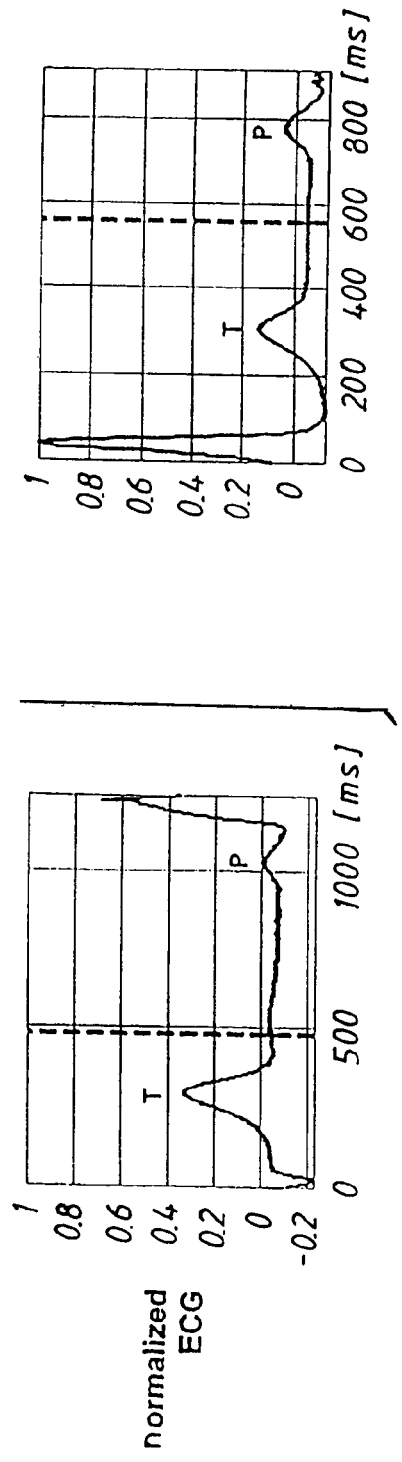
Figure 4C:
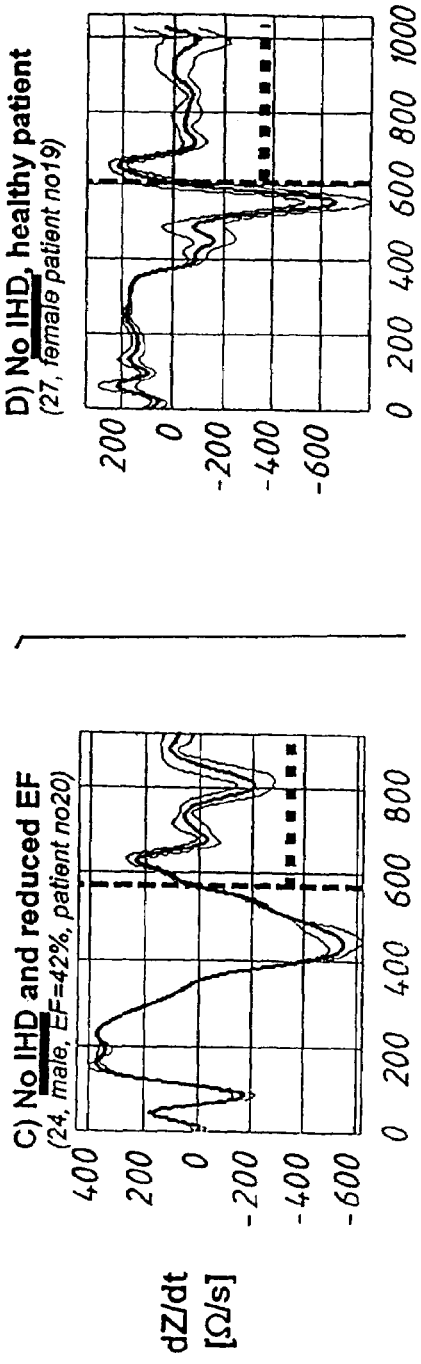
Figure 4D:
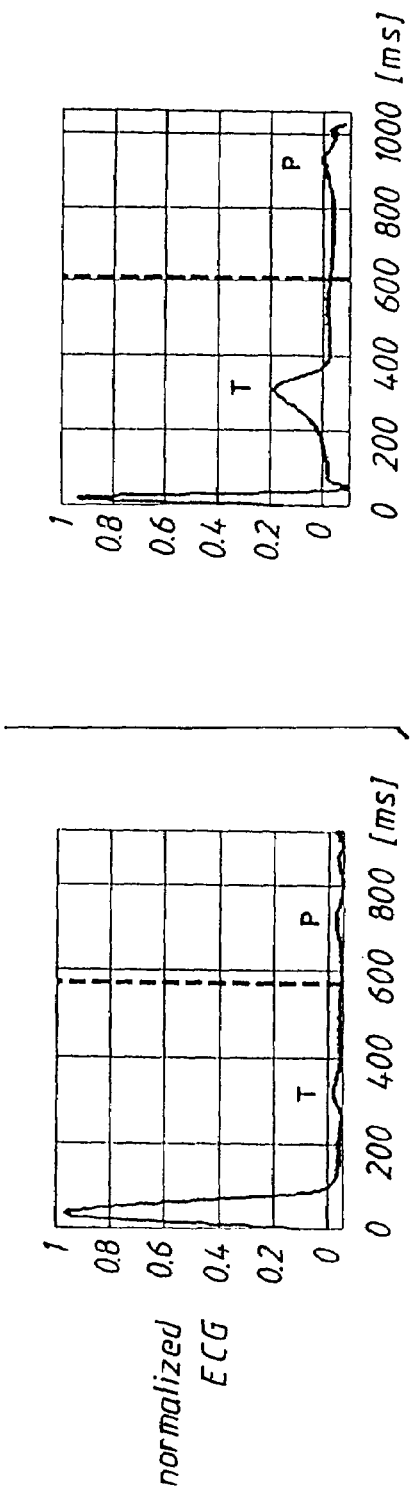

FIGS. 2A, 2B, 2C and 2D show results of right ventricular impedance measurements in four humans. FIG. 2A is for a 73-year-old male, suffering from IHD and having a normal ejection fraction EF of 70% (patient number 14). FIG. 2B is for a 67-year-old male, suffering from IHD and having a reduced EF of 35% (patient number 6). FIG. 2C is for a 24 year old male, having no IHD and reduced EF of 42% (patient number 20). FIG. 2D is for a healthy 27-year-old female (patient number 19).

AC impedance measurements were performed using measuring catheters of type USCI Baid EP. Current was injected between a tip electrode positioned in right ventricular apex and a ring separated 10 mm from the tip. The resulting voltage response was measured between the same two electrodes.

In each of FIGS. 2A, 2B 2C and 2D the average value and the standard deviation for the measured impedance Z, the corresponding quantities for the first time derivative of the impedance curves dZ/dt, as well as a normalized ECG as a function of time are shown.

These measurements can be used to discriminate IHD from non-IHD by using pattern recognition by comparing the post-notch impedance curve or its time derivative to "normal" impedance templates or "normal" first time derivative templates.

FIGS. 2A–2D it can be seen that for humans suffering from IHD the measured impedance curve Z exhibits, after the notch indicated in FIG. 2 by a vertical dashed bold line, a plateau followed by the steep decrease. The impedance curve Z for a non-IHD human has no such plateau and decrease, cf. FIG. 2C and FIG. 2D.

In the corresponding dZ/dt curves IHD manifests itself as a distinct minimum in the post-notch region, encircled in FIG. 2A and FIG. 2B. Such a distinct minimum cannot be traced in the dZ/dt curves from non-IHD humans.

The measured Z and dZ/dt curves can be used for creating loops as described in the above mentioned PCT/SE01/02615 and IHD be detected by analyzing that part of the resulting loops which correspond to the post-notch portion of the impedance curves.

FIGS. 3A and 3B show the average impedance curve and the standard deviation from measurements in a number of cardiac cycles for a IHD patient (FIG. 3A) and a healthy patient (FIG. 3B).

It can be seen from FIGS. 3A and 3B that patients having IHD, independent of EF status, exhibit a plateau after the notch in the impedance curve Z followed by a dominating, distinct decrease coinciding with atrial contraction. The position of the notch is marked in FIGS. 3A and 3B by a dashed, vertical, bold line. As discussed above this decrease corresponds to the compensation by the atrium for the reduced passive filling of the ventricle of these patients.

The impedance curve Z for non-IHD patients may also have a plateau like portion after the impedance notch and atrial contraction may also be seen as a decrease in the impedance curve, but not as clear and dominating as for IHD patients.

Discriminating IHD patients from non-IHD patients can be accomplished by calculating a ZIHD-index=$\Delta Z_1/\Delta Z_2$.

As can be seen from FIGS. 3A and 3B $$\Delta Z_1 = Z_{max} - Z_{plateau}$$

where $Z_{max}$ denotes the maximum value of the impedance curve in the notch region and $Z_{plateau}$ the impedance value of the post-notch plateau, and $$\Delta Z_2 = Z_{plateau} - Z_{min}$$

where $Z_{min}$ denotes minimum value in the decrease following the plateau.

This index ZIHD is smaller for IHD patients (FIG. 3A), than for non-IHD patients (FIG. 3B).

The maximum value $Z_{max}$ appears in FIGS. 3A and 3B before the notch, however sometimes a maximum value of the impedance after the notch can be used. For some patients it can be suitable to use as maximum value $Z_{max}$ an average value of a maximum value occurring before the notch and a maximum value occurring after the notch, cf. FIG. 2A.

The plateau value $Z_{plateau}$ preferably is determined as an average value of the measured impedance curve in a predetermined time window after the notch. The length of this window can suitably be in the range of 100–150 msec and the location of the time window can be delayed more or less after the notch depending on the appearance of the impedance curve in the vicinity of the notch (occurrence of possible overshoots, etc.). The time from the occurrence of the notch to the steep decrease in the measured Z curve is depending on the heart rate, the length of the plateau decreasing with increasing heart rate. This must also be taken into consideration when determining the length of the time window.

FIGS. 4A, 4B, 4C and 4D show the dZ/dt curves and the normalized ECGs of FIGS. 2A–2D. From FIG. 4A–4D it can be seen that by using a suitably selected discriminating threshold level, indicated by a horizontal dashed bold line after the notch in the dZ/dt-curves, the large down-slope coinciding with atrial activity for IHD patients can be correctly detected. Thus for the subjects of FIGS. 4A and 4B the dZ/dt curves decrease below the marked threshold value indicating IHD, whereas for the subjects of FIGS. 4C and 4D the dZ/dt curves never reach this threshold, indicating non-IHD.

FIG. 5 shows a preferred embodiment of the monitor according to the invention in the form of a block diagram. The measured impedance Z, block 1, is supplied to a notch detector 3, of the kind described in PCT Application WO 02/43587. The notch detector 3 detects notch existence and timing in the measured impedance curve. The pattern recognition unit 4 detects the shape of the post-notch impedance curve and compares it with a stored predetermined reference or normal impedance curve template.

A differentiating unit is provided to calculate the first time derivative dZ/dt, block 2, which is also supplied to the pattern recognizer 4 for comparison of the shape of the dZ/dt curve in the post-notch portion with a predetermined reference impedance derivative template.

The derivative dZ/dt is also supplied to a dZ/dt marker detector 5 for detecting the large negative dZ/dt-values of IHD patients coinciding with atrial activity after detection of a notch as described above, e.g. by comparing dZ/dt with a predetermined threshold value.

The ZIHD-index calculator 6 calculates the ZIHD-index=$\Delta Z_1/\Delta Z_2$ for use for distinguishing IHD patients from non-IHD patients as described above. With the aid of the ZIHD-index the IHD progression or degree can be monitored. Progressing IHD results in increasing atrial compensation for reduced passive ventricular filling, however, this compensation is possible only to a certain point. With still progressing IHD the atrium will become enlarged and the risk of atrial defibrillation is obvious. By monitoring the ZIHD-index future atrial defibrillation problems can be avoided.

The embodiment shown in FIG. 5 also includes a monitor and diagnostics unit 7 for collecting, analyzing and storing measured data. Sometimes the notch does not appear clearly and might be difficult to detect. Information from previous measurements on the patient in question can in this case be used for locating the decrease in the impedance curve corresponding to atrial activity.

Although modifications and changes may be suggested by those skilled in the art, it is the intention of the inventor to embody within the patent warranted hereon all changes and modifications as reasonably and properly come within the scope of his contribution to the art.

I claim:

1. A monitor for early detection of an ischemic heart disease, comprising:
    an impedance measurement unit, including an electrode arrangement for interacting with a patient to measure an intracardiac impedance and to generate a corresponding impedance signal;
    a notch detector connected to said impedance measurement unit which detects an occurrence of a notch in the impedance signal coincident with entry of blood into a ventricle, with a portion of said impedance signal following said notch being a post-notch impedance curve; and
    a pattern recognition unit, which compares said post-notch impedance curve with a stored reference impedance curve template to obtain a comparison result and to detect an ischemic heart disease from said comparison result.

2. A monitor as claimed in claim 1 wherein said pattern recognition unit compares a shape of said post-notch impedance curve to a shape of said reference impedance curve template.

3. A monitor as claimed in claim 1 comprising a differentiating unit which calculates a time derivative at least of said post-notch impedance curve, and wherein said pattern recognition unit compares a shape of said time derivative of said post-notch impedance curve with a stored reference time-derivative impedance curve template.

4. A monitor as claimed in claim 1 comprising a calculation unit which calculates, for each cardiac cycle, an ischemic heart disease index ZIHD-index, defined by ZIHD-index=$\Delta Z_1/\Delta Z_2$, wherein $\Delta Z_1$ denotes, for each cardiac cycle, a difference between a maximum value of said impedance signal and an impedance value measured in a plateau occurring in said impedance signal after said notch, and wherein $\Delta Z_2$ denotes a difference between said impedance value in said plateau and a minimum value of said impedance signal in a region of decreasing impedance following said plateau in said impedance signal, and an analysis unit supplied with the calculated ZIHD-index for detecting an ischemic heart disease from the calculated ZIHD-index.

5. A monitor as claimed in claim 4 wherein said analysis unit includes a comparator which compares an absolute value of $\Delta Z_1$ with a predetermined $\Delta Z_1$ threshold value for detecting an ischemic heart disease.

6. A monitor as claimed in claim 4 wherein said analysis unit includes a comparator which compares an absolute value of $\Delta Z_2$ with a predetermined $\Delta Z_2$ threshold value for detecting an ischemic heart disease.

7. A monitor as claimed in claim 4 wherein said analysis unit includes a comparator which compares an absolute value of $\Delta Z_1$ with a predetermined $\Delta Z_1$ threshold value and an absolute value of $\Delta Z_2$ with a predetermined $\Delta Z_2$ threshold value, for detecting an ischemic heart disease.

8. A monitor as claimed in claim 4 wherein said maximum value used in said calculation unit is a maximum value located, in each cardiac cycle, in said impedance signal before said notch.

9. A monitor as claimed in claim 4 wherein said maximum value used in said calculation unit is a maximum value located, in each cardiac cycle, in said impedance signal after said notch.

10. A monitor as claimed in claim 4 wherein said maximum value used in said calculation unit is an average value of a maximum value in the impedance signal for a cardiac cycle located before said notch, and a maximum value of the impedance signal for that cardiac cycle located after said notch.

11. A monitor as claimed in claim 4 comprising an averaging unit for forming said plateau impedance value as an average value of said impedance signal in a predetermined time window after said notch.

12. A monitor as claimed in claim 11 wherein, in said averaging unit, a beginning of said time window after said notch is selectable.

13. A monitor as claimed in claim 11 wherein, in said averaging unit, said time window begins at a time in a range between 100 and 150 msec following said notch.

14. A monitor as claimed in claim 4 comprising a differentiating unit which forms a time derivative of said impedance signal and which determines a slope of said region of decreasing impedance from said time derivative, and a comparator which compares said slope with a predetermined slope threshold.

15. A monitor as claimed in claim 1 comprising:
a differentiating unit supplied with said impedance signal for calculating a first time derivative of said impedance signal;
a loop generator connected to said impedance measurement unit and to said differentiating unit for plotting impedance values from said impedance signal relative to related values in said first time derivative to form a loop for each cardiac cycle; and
a comparator connected to said loop generator for comparing said loop with a loop template to obtain a comparison result for detecting an ischemic heart disease dependent on said comparison result.

16. A monitor as claimed in claim 15 wherein said comparator compares a shape of said loop in a portion of said loop corresponding to said post-notch impedance curve, with a corresponding portion of said loop template.

17. A monitor as claimed in claim 1 comprising an averaging unit connected to said impedance measuring unit for forming an average impedance signal from a plurality of impedance signals respectively obtained during a predetermined number of cardiac cycles, and wherein said pattern recognition unit is connected to said averaging unit and compares a post-notch impedance curve in said average impedance signal with said reference impedance curve template.

18. A monitor as claimed in claim 1 comprising:
a differentiating unit supplied with said impedance signal that calculates a first time derivative of said impedance signal;
an averaging unit connected to said differentiating unit which forms an average time derivative from a plurality of first time derivatives of respective impedance signals in a predetermined number of cardiac cycles; and
wherein said reference impedance curve template is a reference impedance derivative template, and wherein said pattern recognition unit is connected to said averaging unit and compares the average time derivative of the post-notch impedance curve in said cardiac cycles with a corresponding portion of said reference impedance derivative template.

19. A monitor as claimed in claim 1 comprising:
a first averaging unit supplied with said impedance signal for determining an average impedance signal from a plurality of impedance signals measured during a predetermined number of cardiac cycles;
a differentiating unit supplied with said impedance signals that calculates a first time derivative of said impedance signals in said cardiac cycles;
a second averaging unit connected to said differentiating unit that forms an average time derivative from the respective first time derivatives in said cardiac cycles;
a loop generator connected to said first averaging unit and to said second averaging unit for plotting said average impedance values against related average time derivatives to form an average loop for each cardiac cycle; and
a comparator that compares said average loop with a predetermined loop template to obtain a comparison result for detecting an ischemic heart disease dependent on said comparison result.

20. A monitor as claimed in claim 19 wherein said first and second averaging units are formed by a single averaging unit.

21. A monitor as claimed in claim 1 wherein said electrode arrangement comprises a bipolar ventricular electrode having an electrode tip and a ring, and wherein said impedance measuring unit measures said impedance signal between said electrode tip and said ring.

22. A monitor as claimed in claim 1 comprising a housing containing said impedance measurement unit, said notch detector, and said pattern recognition unit, and wherein said electrode arrangement comprises a unipolar ventricular electrode having an electrode tip, and wherein said impedance measuring unit measures said impedance signal between said electrode tip and said housing.

* * * * *